United States Patent [19]

Rich et al.

[11] Patent Number: 5,060,643
[45] Date of Patent: Oct. 29, 1991

[54] BREATH-ACTIVATED INHALATION DEVICE

[75] Inventors: Michael Rich, Danbury, Conn.; Paul Mulhauser; Douglas M. Spranger, both of New York, N.Y.

[73] Assignee: Tenax Corporation, Danbury, Conn.

[21] Appl. No.: 563,927

[22] Filed: Aug. 7, 1990

[51] Int. Cl.⁵ .............................................. A61M 11/00
[52] U.S. Cl. ............................ 128/200.23; 128/200.14
[58] Field of Search ........................ 128/200.23, 200.14

[56] References Cited

U.S. PATENT DOCUMENTS

| | | | |
|---|---|---|---|
| 3,456,644 | 7/1969 | Thiel | 128/173 |
| 3,456,646 | 7/1969 | Phillips et al. | 128/173 |
| 3,565,070 | 2/1971 | Hanson | 128/173 |
| 3,636,949 | 1/1972 | Kropp | 128/173 R |
| 3,732,864 | 5/1973 | Thompson et al. | 128/173 R |
| 3,789,843 | 2/1974 | Armstrong et al. | 128/173 |
| 3,814,297 | 6/1974 | Warren | 222/402.13 |
| 3,818,908 | 6/1974 | Phillips | 128/173 |
| 3,826,413 | 7/1974 | Warren | 222/402 |
| 4,137,914 | 2/1979 | Wetterlin | 128/203 |
| 4,291,688 | 9/1981 | Kistler | 128/200.23 |
| 4,292,966 | 10/1981 | Mono et al. | 128/200.23 |
| 4,352,789 | 10/1982 | Thiel | 424/46 |
| 4,414,972 | 11/1983 | Young et al. | 128/200.23 |
| 4,446,862 | 5/1984 | Baum et al. | 128/203.15 |
| 4,470,412 | 9/1984 | Nowacki et al. | 128/200.18 |
| 4,509,515 | 4/1985 | Altounyan et al. | 128/200.23 |
| 4,534,343 | 8/1985 | Nowacki et al. | 128/200.23 |
| 4,576,157 | 3/1986 | Rahusprasad | 128/200.23 |
| 4,592,348 | 6/1986 | Waters, IV et al. | 128/200.23 |
| 4,624,251 | 11/1986 | Miller | 128/200.14 |
| 4,635,627 | 1/1987 | Gam | 128/200.14 |
| 4,648,393 | 3/1987 | Landis et al. | 128/200.23 |
| 4,664,107 | 5/1987 | Wass | 128/200.23 |
| 4,703,753 | 11/1987 | Bordoni et al. | 128/200.14 |
| 4,796,614 | 1/1989 | Nowacki et al. | 128/200.14 |
| 4,819,834 | 4/1989 | Thiel | 222/355 |
| 4,834,083 | 5/1989 | Byram et al. | 128/200.23 |
| 4,852,561 | 8/1989 | Sperry | 128/200.23 |
| 4,860,740 | 8/1989 | Kirk et al. | 128/203.15 |

FOREIGN PATENT DOCUMENTS 1917911 10/1970 Fed. Rep. of Germany.
1270272 4/1972 United Kingdom.

Primary Examiner—Edgar S. Burr
Assistant Examiner—Kimberly L. Asher
Attorney, Agent, or Firm—Kramer, Brufsky & Cifelli

[57] ABSTRACT

Upon inhalation of air from the interior of a housing, a flexible diaphragm-type valve exposed to the ambient air surrounding the housing is moved inwardly due to the difference in ambient air pressure to that in the housing to expose the interior of the housing to the ambient air which is then drawn into the housing. Upon movement of the valve, it strikes a lever connected to a toggle linkage arrangement, causing the lever to pivot to break the toggle linkage, enabling a coil spring to extend and move a dispensing nozzle into contact with the valve stem of a medicant-containing, aerosol valve actuated, bottle. The valve stem is urged upwardly by the nozzle and moved into the interior of the bottle dispensing a dose of the medicant to be mixed with the inhaled air, which is inhaled by the user. The bottle is housed in a storage chamber having a reciprocably sliding cap mounted therein which can be manually moved to reset the nozzle and toggle linkage in its locked position, to prevent the nozzle from opening the aerosol valve and ready the device to dispense a dose of medicant once inhalation is repeated.

3 Claims, 5 Drawing Sheets

BREATH-ACTIVATED INHALATION DEVICE

BACKGROUND OF THE INVENTION

1. Field of the Invention

This invention relates to a device for dispensing a dose of a medicant, and more particularly, a medicant dispensing device which is activated by the user upon inhalation of air from the interior of the housing of the device.

2. Description of the Prior Art

U.S. Pat. Nos. 3,456,644; 3,456,646; 3,565,070; 3,636,949; 3,732,864; 3,789,843; 3,814,297; 3,826,413 4,648,393; 4,664,107; and 4,648,393 all disclose a breath-activated inhalation device wherein a dose of a medicant is dispensed from an aerosol container to be mixed with air drawn into the housing of the inhalation device upon inhalation by a user. Each of these patents illustrate a device wherein the air drawn from the exterior of the housing upon inhalation by the user opens a valve and flows through an opening normally closed by the valve into the interior of the housing. Movement of the valve in turn causes movement of a linkage arrangement to permit the aerosol container to drop or be moved downwardly to open the aerosol valve of the container so that a measured dose of a medicant can be inhaled with the air entering the housing.

While the inhalation-actuated aerosol dispensing devices illustrate some of the concepts involved in the present invention, the toggle linkage arrangement used in the present invention for locking and unlocking the device, along with a nozzle movable relative to a stationary medicant container to accommodate the dispensing of the medicant from the container is different and ensures activation only upon inhalation by a user.

SUMMARY OF THE INVENTION

Upon inhalation of air from the interior of a housing, a flexible diaphragm-type valve exposed to the ambient air surrounding the housing is moved inwardly due to the difference in ambient air pressure to that in the housing to expose the interior of the housing to the ambient air which is then drawn into the housing. Upon movement of the valve, it strikes a lever connected to a toggle linkage arrangement, causing the lever to pivot to break the toggle linkage, enabling a coil spring to extend and move a collar into contact with a dispensing nozzle which in turn is in contact with a spring-biased valve stem of a medicant-containing, aerosol valve actuated, bottle. The valve stem is urged upwardly by movement of the nozzle under the urging of the collar. The valve stem is moved into the interior of the bottle until the spring pressure on the valve stem caused by compression of the spring exceeds the pressure exerted by contact of the nozzle, causing the dispensing of a dose of the medicant to be mixed with the inhaled air, which is inhaled by the user. When the internal spring pressure on the valve stem exceeds the pressure exerted by the nozzle, the valve stem will be pushed out of the bottle returning the nozzle to its initial position, closing the valve in the interior of the bottle to preclude further dispensing of the medicant until the cycle is repeated.

The bottle is housed in a storage chamber having a reciprocably sliding cap which can be manually moved downwardly to recock the device. The cap, upon downward movement, contacts the top of the collar to move the toggle linkage back to its initial linear or locked condition to reset the lever and lock the collar in its initial position beneath the nozzle until the inhalation cycle is repeated.

BRIEF DESCRIPTION OF THE DRAWINGS

Further objects and advantages of the invention will become apparent from the following specification and claims, and from the accompanying drawings, wherein:

DETAILED DESCRIPTION OF THE PREFERRED EMBODIMENT

Figure 1:
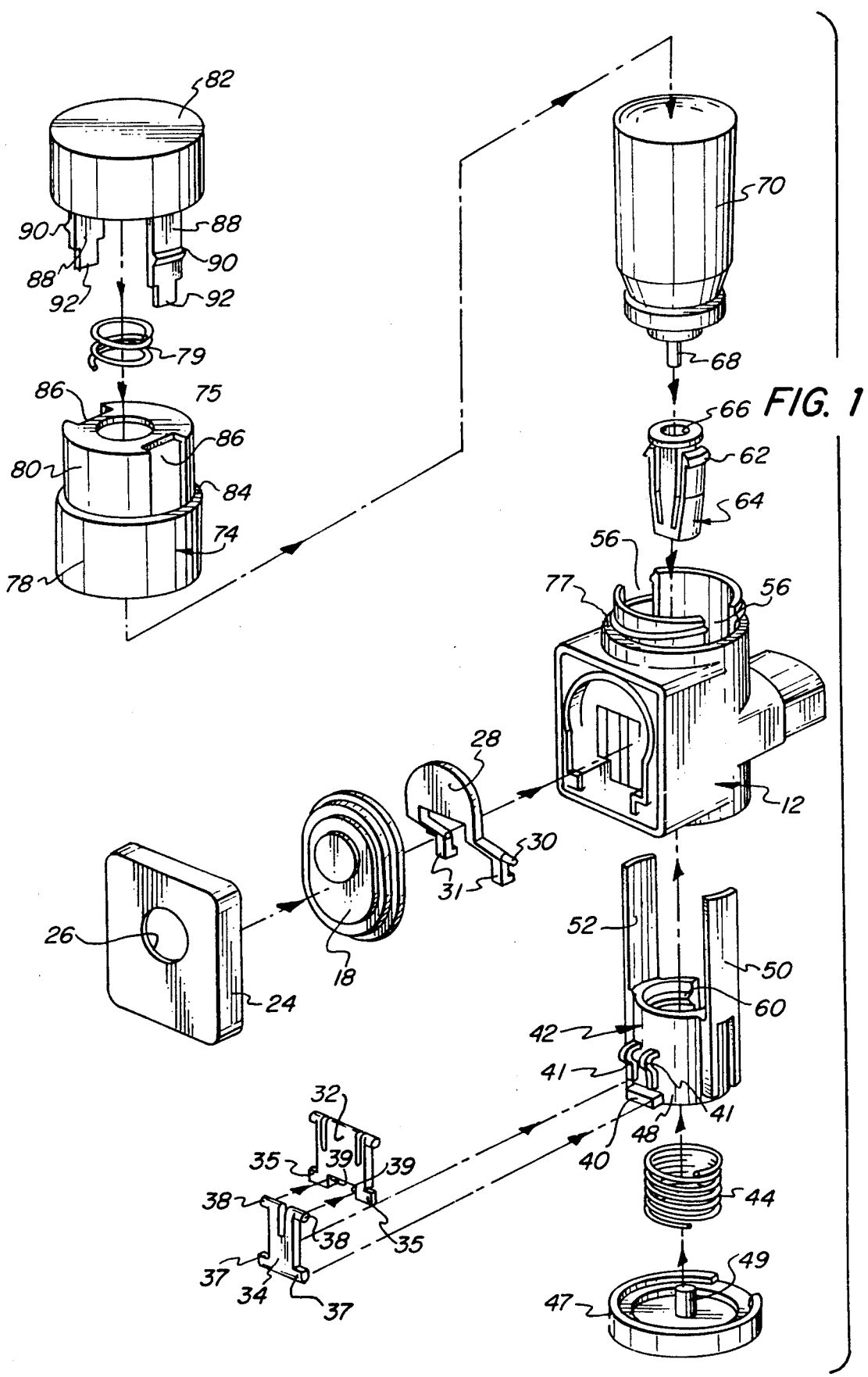
FIG. 1 is an exploded perspective view of the breath-activated inhalation device of the present invention.

Referring now to the drawings in detail wherein like numerals indicate like elements throughout the several views, the breath-activated inhalation device of the present invention is illustrated by the numeral 10.

Figure 4:
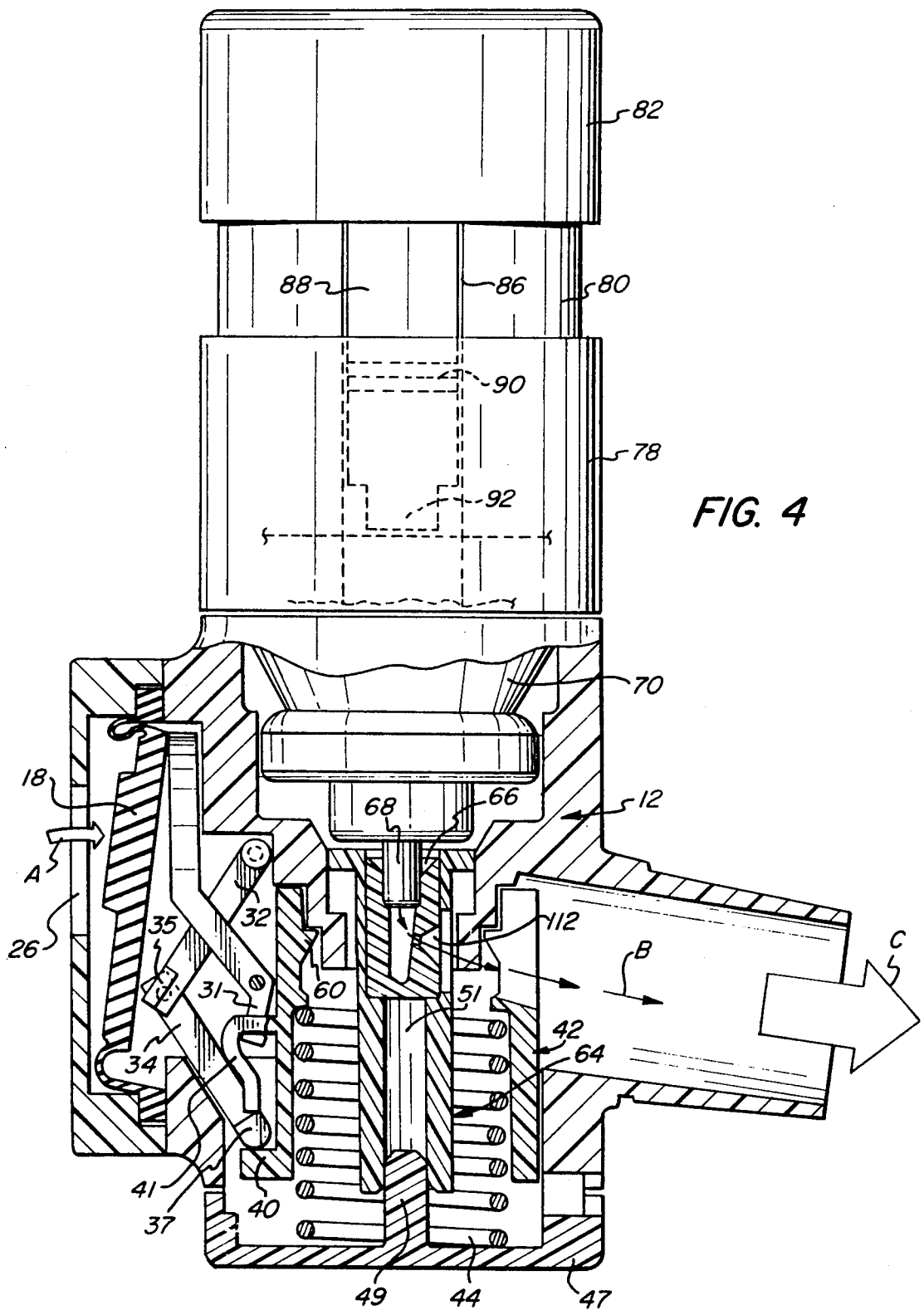
FIG. 4 is a view similar to FIG. 2 with certain portions of the breath-activated inhalation device illustrated in side elevation for purposes of illustration and further indicating the position of the components of the device upon being activated by a user upon inhalation, as indicated by the arrows.

The device 10 includes a housing 12 which is generally cylindrical in shape. The housing 12 has a lateral extension 14 for insertion in the mouth of a user. A cover 16 can be removed to expose the interior of the extension 14. The opposite side of the housing includes a flexible diaphragm-type valve 18. Valve 18 is flexible and is pivoted at opposite ends between surfaces 20 and 22 on the housing 12 and a cap 24 mounted on the housing and having an opening 26 for receiving a portion of the flexible diaphragm-type valve 18. The diaphragm-type valve 18 is thicker on its upper median portion so that it will pivot about surfaces 22,22 at the bottom of the housing 12 and cap 24 (e.g., as shown in FIG. 4) when a force is exerted on the valve portion which extends through opening 26.

Figure 2:
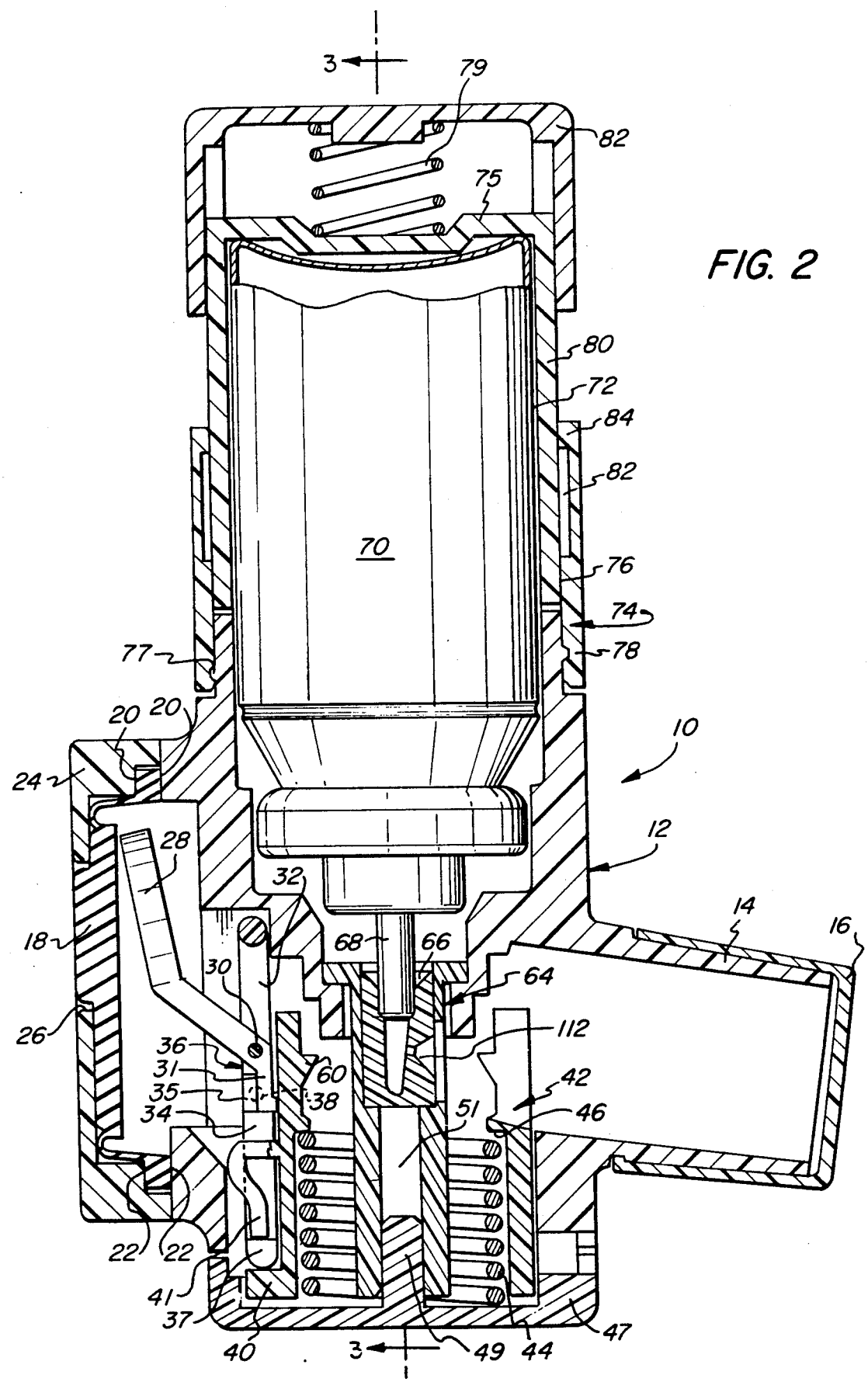
FIG. 2 is a longitudinal cross-section of the assembled breath-activated inhalation device of the present invention in cocked condition ready for use.

The rear surface of the diaphragm-type valve 18 is in contact with a lever or trigger 28 pivotably connected by an axle 30 to an interior surface of housing 12. A pair of arms or links 32,34 of a toggle linkage arrangement 36 are pivoted to each other along the axis of a pair of pintles 38 on link 34 received in openings 39 in link 32 and are normally in an aligned, linear fashion as illustrated in FIG. 2. Upper arm or link 34 has laterally extending tabs 35 disposed behind and in contact with downwardly extending feet 31 on lever 28 in the assembly. The bottom link 34 of the toggle link pair 36 has a pair of laterally extending tabs 37 seated between a platform 40 of a nozzle activation device or collar 42, and the bottom surfaces of a pair of substantially inverted L-shaped hooks 41 on a cylindrical surface 48 of collar 42, thus forming a captive pivot axis.

The collar 42 is biased upwardly by a coil spring 44 seated between an internal shoulder 46 on the collar 42 and a cap 47 mounted on the bottom of housing 12 and having a central upright pin 49 received in a central bore 51 of a movable nozzle, generally designated by the numeral 64.

The cylindrical body portion 48 of collar 42 has a pair of spaced upright wings 50,52 connected to an annular flange 54. A wing 50,52 is received in sliding engagement in one of the keyways or slots 56 formed on diametrically opposed portions of the interior surface of the housing 12.

The collar or nozzle activation device 42 also includes an internal annular flange 60 in seated engagement with an annular flange 62 on movable nozzle 64. The nozzle 64 includes an opening 66 in communication with a valve stem 68 on a medicant-dispensing container 70 which is seated in movable nozzle 64. The valve stem 68 of the container 70 is linearly movable upon contact by the nozzle activation device or collar 42.

The medicant-dispensing container 70 is housed within a storage chamber 72. The storage chamber 72 is formed by a cover 74 threadedly connected to the threads 77 on the top of housing 12. The cover 74 is cylindrical in shape and includes a lower portion 78 having a cylindrical bore 76 slidably receiving an upper portion 80 having a top surface 75 in contact with a coil spring 79 disposed between the top surface 75 and a linearly displaceable cap 82 slidably disposed on the top of the reduced diameter upper portion 80 of cover 74. The upper portion 80 is seated on the top of housing 12.

The lower portion 78 of cover 74 has an annular slot 82 formed therein terminating in a top flange 84. The upper portion 80 has a pair of diametrically opposed slots 86, each receiving a depending slide 88 extending downwardly from diametrically opposed portions of cap 82. Each slide 88 has an integral, horizontal arcuate ridge 90 snapped under flange 84 for sliding engagement against the wall of annular slot 82 in lower portion 78 of cover 74. The flange 84 precludes disengagement of cap 82 and slides 88 from the cover 74.

In use, the device 10 is first cocked or set to use by pressing downwardly on cap 82 compressing coil spring 79 and releasing the cap 82 which is returned to its initial position by spring 79. Downward movement of cap 82, however, causes downward movement of slides 88 in slots 86 of upper portion 80 of cover 74. The slots 86 in upper portion 80 of cover 74 are aligned with slots 56 on the interior surface of housing 12, which receive the wings 50,52 of collar or nozzle activation device 42. Downward movement of slides 88 in slots 86 causes the feet 92 of the slides to contact the top of one of the wings 50,52 to move the wings and collar 42 downwardly against the upward bias of the coil spring 44 to the position shown in FIGS. 2 and 3. Hooks 41 contact tabs 37 on lower link 34 of the toggle link arrangement 36 and cause the links 32 and 34 to pivot relative to each other to a linear locked condition, precluding upward movement of collar 42 under the urging of coil spring 44. Tabs 35 on upper link 32 contact feet 31 on lever 28 to cause the lever to pivot about axle 30 in a counterclockwise manner as viewed in FIG. 2, to contact and close diaphraghm-type valve 18 by positioning it in opening 26 in cap 24. Downward movement and locking of collar 42 by the toggle link arrangement 36 also positions flange 60 beneath flange 62 on movable nozzle 64, as the interior surface of the flange can slide over the exterior surface of flange 62 camming its arms 63 inwardly about an annular slot 65 until it passes beneath flange 62, wherein the arms 63 spring outwardly to position the flange 60 beneath flange 62. The device is now ready for use and the elements are in the position illustrated in FIGS. 2 and 3.

Figure 3:
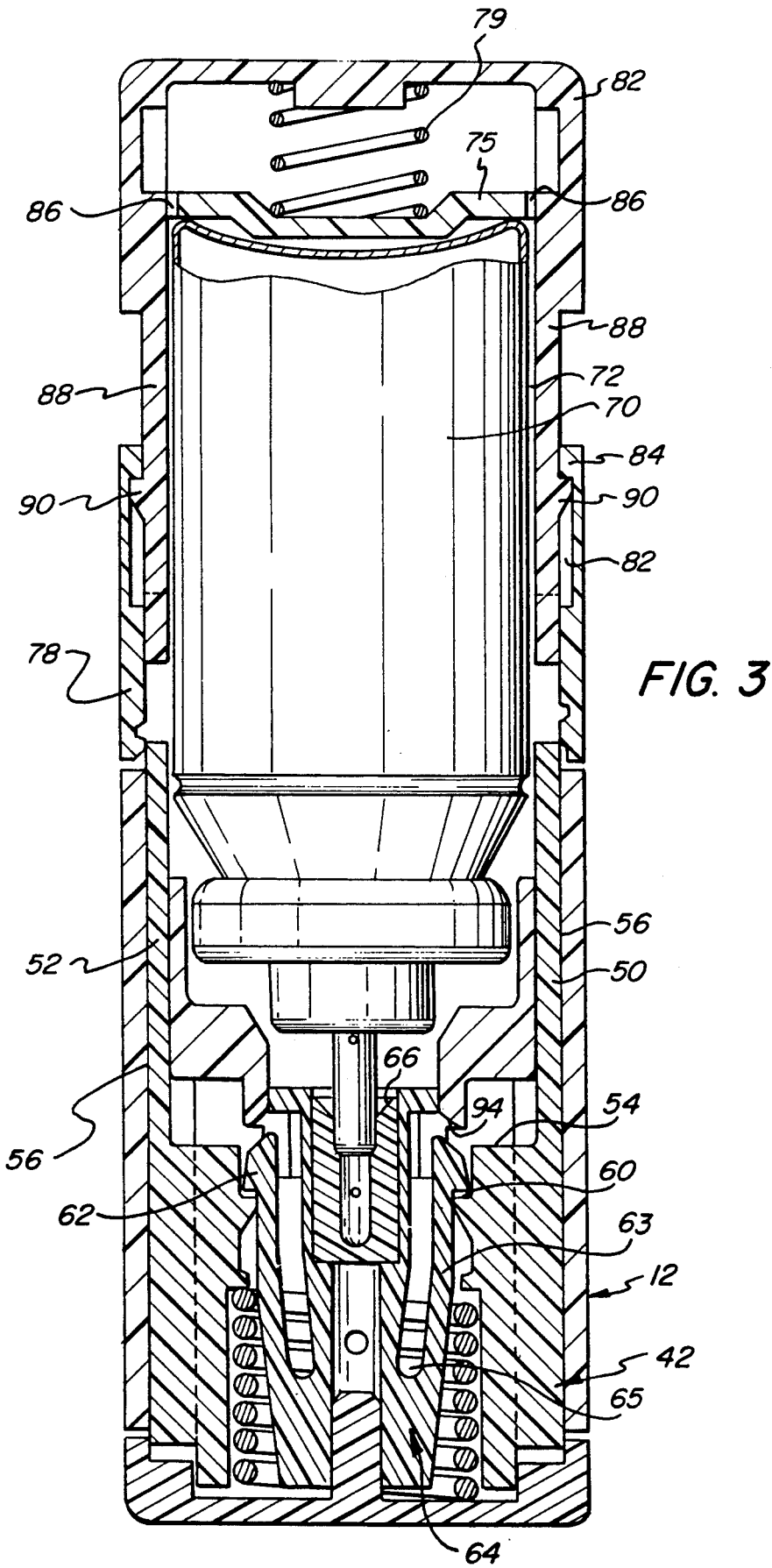
FIG. 3 is a cross-sectional view taken substantially along the plane indicated by line 3—3 of FIG. 2.

In the cocked position, as shown in FIG. 3, the aerosol container valve stem 68 has moved down under the urging of a compressed spring 100 held captive in aerosol valve assembly 102, between an enlarged flange 104 on stem 68 and a valve plate 106. The stem 68 slides through a second valve plate 108 disposed in the bottom of valve assembly 102 to position an orifice 110 outside of container 70 to preclude the flow of medicant from the interior of container 70 through orifice 110 and stem 68 into the bore 66 in nozzle 64 and out a dispensing orifice 112 into mouthpiece 14.

With device 10 locked and the various elements in their position illustrated in FIGS. 2 and 3, the device is ready for insertion into the mouth of a user, who inhales. Upon inhalation of the air from the interior of housing 12 through mouthpiece 14, the flexible diaphragm-type valve 18 exposed to the ambient air through opening 26 in cap 24 is moved inwardly and pivots about lower facing surfaces 22 on the cap 24 and housing 12 to the position indicated in FIG. 4, due to the difference in ambient air pressure to that in the housing 12. The interior of housing 12 is exposed to the ambient air which is then drawn into the housing through opening 26 as indicated by arrow A. Upon movement of the valve 18, it strikes lever 28, causing it to pivot in a clockwise direction as indicated in FIG. 4. Feet 31 on lever 28 push tabs 35 causing link 32 to rotate in a clockwise direction and link 34 to rotate in a counterclockwise direction as viewed in FIG. 4 to break the toggle lock. This enables the coil spring 44 to extend and move the nozzle activation device or collar 42 upwardly relative to the housing 12 with wings 50,52 sliding in slots 56. Flange 60 on collar 42 engages flange 62 on nozzle 64 and raises the nozzle to the position indicated in FIG. 5, causing the top of the nozzle and arms 63 to cam inwardly along an annular camming surface 94.

The aerosol valve stem 68 of the medicant-containing bottle 70 seated in nozzle bore 66 is moved upwardly against the force of spring 100 held captive in aerosol valve assembly 102. Upward movement of the stem 68 enables it to slide through plate 108 to position orifice 110 in the stem 68 in the interior of container 70 enabling medicant to flow through the orifice 110 and stem 68 into the bore 66 in the interior of movable nozzle 64 and out opening 112 as indicated by arrows B in FIG. 4 to mix with inhaled air to be ingested by the user through mouthpiece 14 as indicated by arrow C. A dose of the medicant is thus dispensed to the mouth of the user, until the force on compressed spring 100 is sufficient to overcome the upward pressure exerted by the nozzle 64 on the valve stem 68. When the spring pressure on the valve stem exceeds the pressure exerted by the nozzle, the valve stem will be pushed out of the bottle 70, returning the nozzle 64 to its initial position, closing the valve assembly 102 in the interior of the bottle to preclude further dispensing of the medicant until the cycle is repeated.

Figure 5:
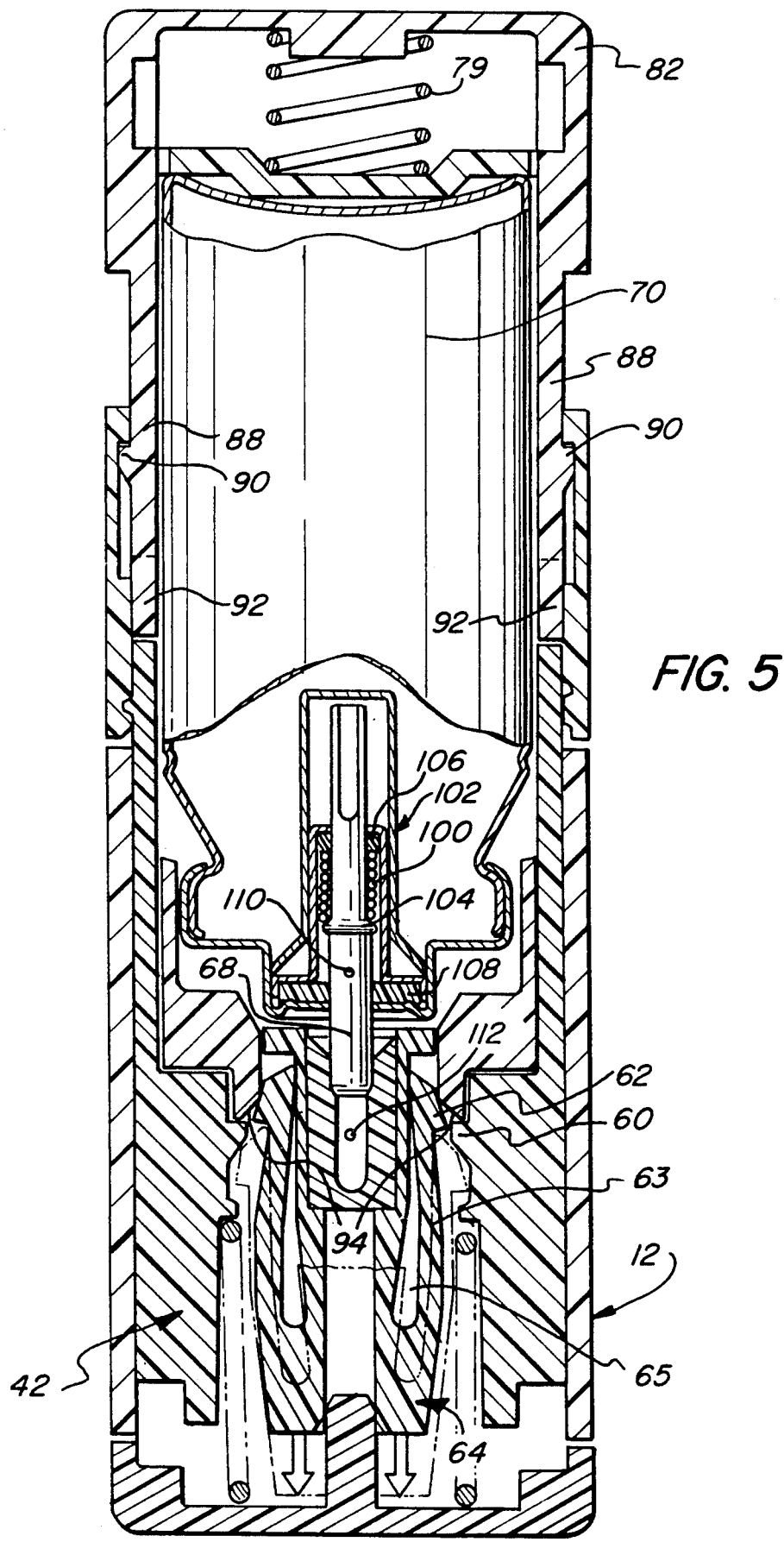
FIG. 5 is a view similar to FIG. 3 but illustrating the position of the elements of the device upon activation by inhalation of the user and further illustrating the manner of returning the device to a cocked, reset position ready for reuse.

When the valve stem 68 received in orifice 66 of nozzle 64 moves downwardly to close the valve in the aerosol container 70 and pushes the nozzle downwardly, as indicated by the arrows in FIG. 5, the nozzle arms 63 expand laterally as it clears an annular camming surface 94 in the interior of housing 12 and flange 60 on collar 42, as illustrated in the dotted line position of the nozzle 64 in FIG. 5. When the device is recocked by pushing downwardly on cap 82, flange 60 on collar 42 will be placed beneath flange 62, corresponding to the full line position in FIG. 3.

When cap 82 is pushed downwardly on cover 74 to recock the device 10 and return the elements of the device to their position indicated in FIGS. 2 and 3, the device is again ready to dispense a dose of a medicant upon inhalation of the user through mouthpiece 14. Preferably, this should be done just prior to inhalation by the user to preclude accidental dispensing of the medicant.

What is claimed is:

1. A fluid dispensing device comprising:

a housing containing a medicant container adapted to be activated by movement of a valve against the bias of a captive spring to dispense a quantity of medicant:

said housing having a mouthpiece for insertion within the mouth of the user;

a flexible diaphragm-type valve means having opposite ends mounted in the interior of said housing and normally closing said housing to the ambient atmosphere, but exposing the housing in response to a difference in air pressure on either side of said valve means induced by inhalation of air from the interior of said housing by a user through said mouthpiece;

a rotatable lever in contact with the rear of said diaphragm-type valve;

a movable nozzle adapted to move into pressure contact with said valve on said medicant-container bottle to open the valve enabling the dispensation of a quantity of medicant after which the valve is closed, and upon closing of said valve said movable nozzle being returned to a non-pressure contact position with said valve, said nozzle including a plurality of upright spring arms, each spring arm having an enlarged camming head;

nozzle activation means for moving said nozzle into pressure contact with said valve on said medicant-container bottle to open said valve by contact with and beneath said enlarged camming head of said spring arms on said nozzle, which upon movement being imparted to said camming heads on said spring arms, said spring arms will contact a fixed abutment and will collapse towards each other with frictional braking contact with said abutment as the nozzle continues into pressure contact with said valve and then allowing said nozzle to be returned to its non-pressure contact position beneath said nozzle activation means by movement of said valve caused by the captive spring in said medicant container against the frictionally braked spring arms of said nozzle;

spring means for normally urging said nozzle activation means to move said nozzle into pressure contact with said valve on said medicant-container bottle;

toggle linkage means between said nozzle activation means and lever for normally locking said nozzle activation means against movement while compressing said spring means beneath said nozzle activation means, but pivotable to a nonlocking position upon rotation and contact by said lever permitting movement of said nozzle activation means under urging of said spring means to move said nozzle into pressure contact with said valve;

whereby upon inhalation of a user through said mouthpiece, said diaphragm-type valve will open to cause said lever to rotate to break and pivot said toggle linkage to enable said nozzle activation means to move said nozzle into pressure contact with said valve to open said valve of said medicant-containing bottle to dispense a dose of a medicant mixed with inhaled air through said mouthpiece, until said valve closes and said nozzle is returned to a non-pressure contact position with said valve; and means on said housing for resetting said toggle linkage means to lock said nozzle activation means against movement, said means including:

reciprocably slidable cap means on said housing for contact with said nozzle activation means to push said nozzle activation means away from the valve on said medicant-container bottle and beneath the camming heads on said spring arms on said nozzle by overriding the enlarged camming heads on the top of each spring arm of said nozzle while simultaneously causing said nozzle activation means to pivot said toggle linkage means to its locking position.

2. The fluid dispensing device of claim 1 including:

contact means on said nozzle activation means for pivotably mounting said toggle linkage means for movement between an unlocked and locked position.

3. The fluid dispensing device of claim 2 including:

tab means on said toggle linkage means for contact with said lever to rotate the same to close said diaphragm-type valve means in response to return of said toggle linkage means to its locked position and to respond to rotation of said lever upon opening of said diaphragm-type valve means to cause said linkage means to pivot to an unlocked position, permitting movement of said nozzle activation means.

* * * * *